(12) United States Patent
Stenzel et al.

(10) Patent No.: US 10,172,990 B2
(45) Date of Patent: Jan. 8, 2019

(54) DIALYSIS MACHINE WITH AN INTEGRATED DIALYZER COUPLING

(71) Applicant: B. BRAUN AVITUM AG, Melsungen (DE)

(72) Inventors: Bruno Stenzel, Muenden (DE); Sebastian Broegger, Knuellwald (DE); Uta Ludwig, Wehretal (DE)

(73) Assignee: B. BRAUN AVITUM AG, Melsungen (DE)

( * ) Notice: Subject to any disclaimer, the term of this patent is extended or adjusted under 35 U.S.C. 154(b) by 45 days.

(21) Appl. No.: 15/346,091

(22) Filed: Nov. 8, 2016

(65) Prior Publication Data

US 2017/0143885 A1 May 25, 2017

(30) Foreign Application Priority Data

Nov. 23, 2015 (DE) .................. 10 2015 120 218

(51) Int. Cl.
*A61M 1/16* (2006.01)
*A61M 1/34* (2006.01)

(52) U.S. Cl.
CPC .......... *A61M 1/1652* (2014.02); *A61M 1/168* (2013.01); *A61M 1/1621* (2014.02); *A61M 1/34* (2013.01); *A61M 1/3417* (2014.02); *A61M 2205/11* (2013.01); *A61M 2205/505* (2013.01); *A61M 2209/082* (2013.01)

(58) Field of Classification Search
CPC .. A61M 1/1621; A61M 1/1652; A61M 1/168; A61M 1/34; A61M 1/3417; A61M 2205/11; A61M 2205/505; A61M 2209/082

See application file for complete search history.

(56) References Cited

U.S. PATENT DOCUMENTS

| 6,308,721 | B1 | 10/2001 | Bock et al. |
| 2011/0303598 | A1 | 12/2011 | Lo et al. |
| 2014/0012176 | A1 | 1/2014 | Schaefer et al. |
| 2014/0112828 | A1 | 4/2014 | Grant et al. |
| 2014/0217029 | A1 | 8/2014 | Meyer et al. |

FOREIGN PATENT DOCUMENTS

| DE | 36 42 671 | 6/1988 |
| DE | 198 52 982 | 3/2000 |
| EP | 0 887 100 | 12/1998 |
| WO | WO 01/08722 | 2/2001 |
| WO | WO 2009/039357 | 3/2009 |

OTHER PUBLICATIONS

European Search Report for EP 16 197 524.8 dated Mar. 23, 2017, with translation.
German Search Report for DE 10 2015 120 218.2 dated Aug. 1, 2016, with translation.

*Primary Examiner* — Dirk R Bass
(74) *Attorney, Agent, or Firm* — RatnerPrestia

(57) ABSTRACT

A dialysis machine with machine-internal fluidics for dialysis fluid and a housing that at least partially encapsulates the fluidics, wherein the fluidics comprise an input line for fresh dialysis fluid to a dialyzer and an output line for used dialysis fluid from the dialyzer, each line equipped at their end sides with a connection port for a releasably coupling with the dialyzer, wherein the port of the input line and the port of the output line are each formed as a coupling integrated into the housing.

3 Claims, 1 Drawing Sheet

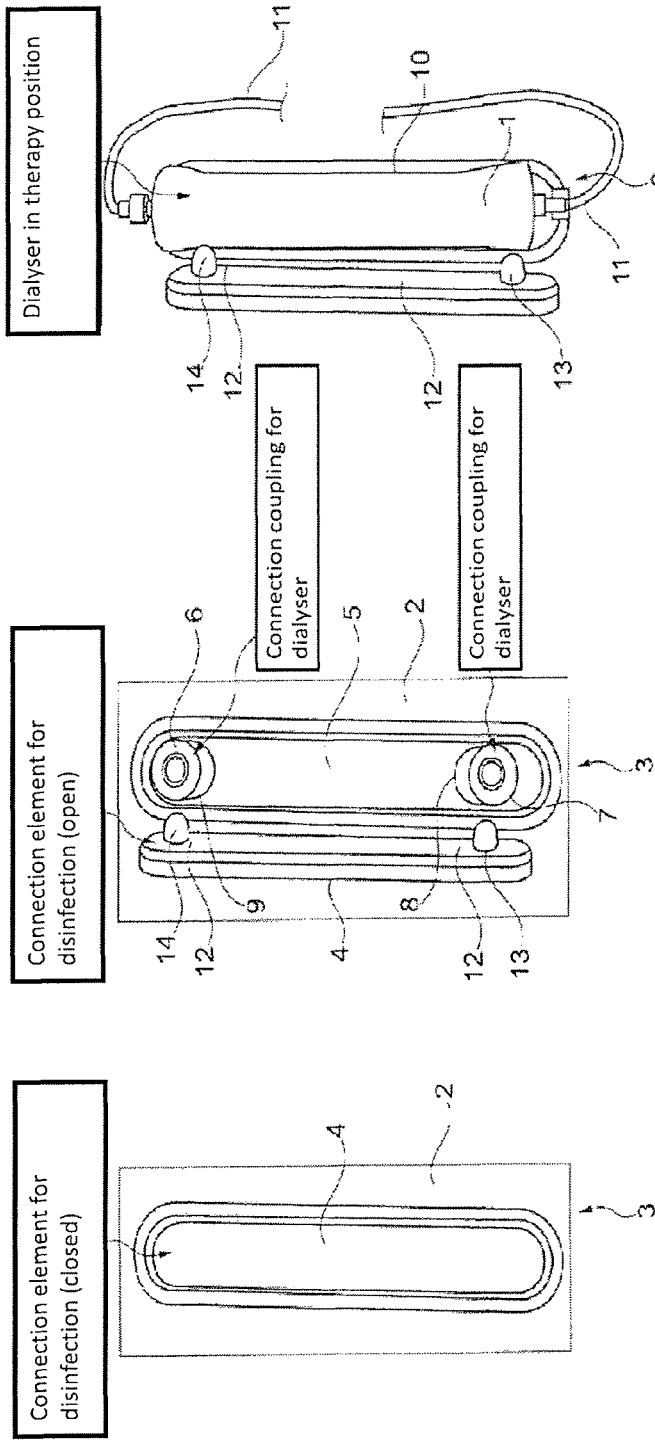

DIALYSIS MACHINE WITH AN INTEGRATED DIALYZER COUPLING

CROSS REFERENCE TO RELATED APPLICATIONS

This application claims priority to German application DE 10 2015 120 218.2 filed Nov. 23, 2015, the contents of such application being incorporated by reference herein.

FIELD OF THE INVENTION

The present invention concerns an extracorporeal blood treatment machine, in particular, a dialysis machine with machine-internal fluidics for blood treatment liquid (fluid), preferably dialysis liquid/dialysate, and a housing (machine housing) encapsulating the fluidics at least in sections or parts, wherein the fluidics comprise a supply line/input line for fresh blood treatment liquid (in the following generally referred to as fresh dialysis fluid) to a filter/dialyzer and a drain line/output line for used blood treatment fluid (in the following generally referred to as used dialysis fluid) from the filter/dialyzer, that are each at their end side(s) equipped with a port/connection port for releasably coupling with the filter/dialyzer.

BACKGROUND OF THE INVENTION

In current dialysis applications, dialysis machines are used, in which a filter/dialyzer in the fashion of a cartridge is affixed preferentially to an outer side of the dialysis machine/the housing of the dialysis machine using a clamp. The dialyzer such affixed to the dialysis machine is subsequently fluidically connected to the internal fluidics of the dialysis machine by connecting tubes/lines/tubing with quick connectors on the one hand with connection ports of the dialyzer intended for that purpose and on the other hand with connection ports of the internals fluidics of the dialysis machine intended for that purpose, which are also located at the housing of the dialysis machine. These tubes carrying dialysis fluid (in the following also referred to as machine-side tubes) are present next/adjacent to blood tubes (in the following also referred to as patient-side tubes) in the proximity of the dialyzer. Because the tubes are rather randomly arranged in the everyday practise and/or can easily tangle up, there is no high user-friendliness. A further disadvantage of the use of dialysis fluid tubes is that due to the length of the tubes and due to their poor thermal insulation characteristics, generally there are temperature losses of the dialysis fluid causing a decrease of the temperature of the blood carried in the patient-side tubes and hence causing a cooling of the patient. A further disadvantage is that in everyday practise disturbances may occur, for example through a pinching off or ripping off of the tubes on beds, tables or other disturbing contours.

SUMMARY OF THE INVENTION

In light of the prior art discussed above, the present invention aims to remove the disadvantages discussed above, specifically to provide an extracorporeal blood treatment machine, preferably a dialysis machine, by which an improvement of the user-friendliness can be effected, that is especially clearly arranged and that allows for one-hand operation by the user. Furthermore, temperature losses of the machine-side blood treatment fluid/dialysis fluid in the input line/output line of the filter, i.e. in the dialyzer input and output line, shall be reduced or avoided.

This technical problem is generally solved by an extracorporeal blood treatment machine with the features of the independent claim. Advantageous modifications of the invention are the subject-matter of the dependent claims.

This technical problem is specifically solved by a blood treatment machine/dialysis machine with machine-internal fluidics for blood treatment fluid/dialysis fluid and a housing (machine housing) encapsulating the fluidics at least in sections or parts, wherein the fluidics comprise an input line for fresh dialysis fluid to a filter/dialyzer and an output line for used dialysis fluid from the filter/dialyzer, that are each at their end side(s) equipped with a connection port for the releasable coupling to/with the filter/dialyzer. According to aspects of the present invention, the connection port of the input line and/or the connection port of the output line is/are each formed as a connection coupling integrated into the housing (machine housing). This means, the connection ports of the blood treatment machine/dialysis machine for the filter/dialyzer are, according to aspects of the present invention, not present anymore at the free ends of machine-external connection tubes. In contrast to that, they (immediately) sit on/in the outer side of the housing wall of the machine housing encasing the fluidics, in such a way that the filter/dialyzer can be (directly) fluidically and in cases also mechanically coupled to the connection ports of the blood treatment machine without the addition of external connection tubes in between.

Put simply, it can be said that the gist of the present invention lies in connecting, especially immediately (without external connection tubes) connecting, the dialysis fluid connection ports of the preferentially cartridge-like filter/dialyzer fluidically via dialyzer couplings/connection couplings integrated into the housing (integrated into the housing wall) of the machine for extracorporeal blood treatment.

According to aspects of the invention at least one connection coupling, preferentially all connection couplings, with which the filter/dialyzer is connected to the internal dialysis fluid lines of the machine, is/are integrated in the machine housing thereof or sit immediately at the outer side of the housing wall of the machine. This means, that the connection couplings are directly or indirectly arranged, affixed or formed in a way to be easily accessible by the user of the machine.

The connection couplings at the machine are preferentially positioned relative to each other according to the geometry and relative position of the dialysis fluid ports of the dialyzer, in such a way that both dialysis fluid ports of the dialyzer can each be simultaneously connected to the respective connection coupling of the machine, preferably by insertion into these, by plugging or screwing. As soon as the two dialysis fluid ports of the dialyzer are arranged in their purposeful manner in their respective connection coupling on the machine-side, the dialysis fluid circuit of the machine is closed. Preferentially, the dialysis fluid ports of the dialyzer are then held with a force sufficient for holding the entire dialyzer at the machine. This means, the machine-side connection couplings are optionally additionally adapted/formed in such a way to be sufficient for mechanically holding the filter/dialyzer at the machine housing during normal filter operation and hence substitute the holding clamps or arms known from the prior art.

According to an embodiment of the invention, at least one of the machine-side connection couplings is arranged in a concave recess/trough/depression formed or arranged in an outer side of the housing, which forms a kind of reception trough for the (cartridge-like) filter/dialyzer. The depth of such a recess is (preferentially slightly/marginally) deeper than the height of the connection coupling(s) in the direction starting from the bottom of the recess, so that the connection coupling(s) is/are completely recessed in the recess and is/are protected. The recess is preferentially formed in terms of its size and geometry in such a way that it forms the reception trough/depression for the dialyzer, the dimensioning/measurement of which is adapted to that exact filter/dialyzer specifically intended for the blood treatment machine. This allows for preventing the use of an unsuitable filter/dialyzer with corresponding unsuitable dimensions. In particular, the dialyzer may be held in the reception recess by friction-fit, form-fit or force-fit. Alternatively or additionally, the housing may also comprise a clamping assembly for holding the dialyzer by clamping.

Furthermore, the machine side and/or dialyzer side connection ports can be not fixedly arranged at the housing wall and dialysis cartridge respectively, but can be equipped with an adaptor or adjustment mechanism for optionally/selectively changing their distances relative to each other. One embodiment of the invention is thus characterized in that in particular the connection couplings integrated into the housing can be positioned relative to each other. Due to couplings that can be positioned relative to each other in such a fashion, the dialysis machine can flexibly be used with dialyzers of differing sizes or designs/configurations. Preferentially, the connection couplings can be positioned relative to each other and can be fixed in position in a corresponding/respective relative position. For this purpose, at least one of the connection couplings can for example be equipped with a clamping or screwing mechanism. When this mechanism is loose, the at least one connection coupling can then be positioned relative to the housing. By locking the mechanism, the at least one connection coupling can be clamped or arrested in the desired fashion to the housing. An especially simple and user-friendly positioning of the connection couplings can be achieved when at least one of the connection couplings is slidably received in the housing in a guide/guiding assembly, for example, in an oblong hole, slot or groove.

According to an embodiment of the invention, the connection couplings integrated into the housing are quick couplings for plugging in/insertion of dialysis fluid connection ports of the dialyzer. It is especially advantageous when they exercise a predetermined and defined holding force suitable for affixing the dialyzer at the housing on the respective dialysis fluid port of the dialyzer. This can occur by a friction-fit and/or form-fit and/or force-fit, for example, via a clamping, a latch mechanism or an interlocking mechanism, that come to effect by the purposeful arrangement of the dialyzer at the machine.

According to a further embodiment, the dialysis machine furthermore comprises a (single/common) lid element for closing, especially for hermetically sealingly closing, of the clamping connection port of the input line (fresh dialysis fluid input line of the dialysis machine) and (at the same time) the connection port of the output line (used dialysis fluid output line of the dialysis machine). The (single) lid element can in particular comprise a fluid passage, via which the connection port of the input line is connected and short-circuited with the connection port of the output line, when the lid element is arranged at the housing of the blood treatment machine so that it closes the connection ports. Such a lid element can be used as a disinfection flap during cleaning and/or sterilization processes of the internal fluidics of the dialysis machine in an especially simple manner.

An especially user-friendly embodiment can provide for a lid element that is movably held at the machine-side housing by a joint or a hinge, in such a way that during a use of the machine (dialysis) with a dialyzer held at the connection couplings it cannot be lost.

With the dialysis machine according to aspects of the invention preferentially many different therapy forms, for example hemodialysis (HD), hemofiltration (HF) or hemodiafiltration (HDF) can be carried out.

In conclusion, the present invention can be summarized in that the dialysis fluid (connection) ports of a dialyzer or at a dialyzer are directly, i.e. without the use of external connection tubes, fluidically connected with dialyzer connection couplings of a machine for extracorporeal blood purification that are integrated into the housing. In the dialysis machine/dialysis device the connection couplings for connecting the dialyzer can be formed/realized as integrated into the housing. For this purpose, the housing can optionally have a recess for the (at least partial) spatial reception of the dialyzer or can be a planar surface. For disinfection, the two connection couplings for the input/output of dialysis fluid to/from the dialyzer can be connected via a connection element (connection port bridge) that can be plugged onto the two connection couplings preferentially from the outside of the machine. In this fashion, the disinfection of the connection components is ensured.

When the dialyzer is connected in/plugged in, the connection element has to be removed. For this purpose it can be movably/deflectably connected at the housing by a joint/hinge. The connection couplings are formed in such a way that an easy interlocking engagement of the dialyzer in/at the connection couplings is possible. In order to be able to use dialyzers of differing sizes, the distance of/between the connection couplings can variably be changed/varied by using an adjustment mechanism or adapter. For relieving the connection sites and for fixing the dialyzer, a fork-like or clamp-like guiding element can be integrated in the assembly for receiving/accepting the weight force of the dialyzer. For the removal of the dialyzer a central decoupler/decoupler assembly/ejecting function may be integrated.

In particular, the following advantages can be effected by the invention:

No exposed tubes project from the device to the dialyzer. This has the effect that the temperature loss of the dialysis fluid between the dialyzer and the (connection) couplings at the end side(s) of the dialysis fluid lines is small, or even does not exist, in contrast to dialyzers that are connected to the dialysis machine by tubes in conventional manner.

The area of the dialyzer is significantly neater and arranged more clearly, in particular, a tangling up of the dialysis fluid tubes with the blood tubes cannot occur.

No tubes can be torn out or pinched off at or by adjacent beds.

The user-friendliness is enhanced by the clear, neater arrangement and optics achieved by the invention.

In an especially advantageous manner a one-hand operation, i. e., a connection and/or ejection of a dialyzer at the dialysis machine, is possible.

Set-up times are significantly shorter than according to the prior art.

BRIEF DESCRIPTION OF THE DRAWINGS

The invention is best understood from the following detailed description when read in connection with the accompanying drawings. Included in the drawings are the following figures:

FIG. 1 shows a schematic top view of the connection area for a dialyzer at a housing of a dialysis machine according to aspects of the invention with closed disinfection flap;

FIG. 2 shows a schematic top view according to FIG. 1 with opened disinfection flap; and FIG. 3 shows a schematic top view according to FIG. 2 with a dialyzer connected to the internal fluidics of the dialysis machine and held at the housing.

DETAILED DESCRIPTION OF THE PREFERRED EMBODIMENTS

FIGS. 1 and 2 each show a connection area for a dialyzer 1 at a housing 2 of a dialysis machine 3. FIG. 2 elucidates the invention with an open disinfection flap (removed connection bridge) 4 and FIG. 1 elucidates the invention with a closed disinfection flap (plugged in connection bridge) 4. A recess in form of a depression/trough 5 is formed in the housing 2 of the dialysis machine 3. The recess 5 is concave when viewed from the outside, that means, it is recessed into the drawing plane of the FIGS. 1 and 2.

In the recess 5, a first connection coupling 6 (in the following simply referred to as first coupling) and a second connection coupling 7 (in the following simply referred to as second coupling) are arranged. These are inserted/accommodated in the oblong holes 8, 9 that are formed at the bottom of the recess 5 and are shown in the figures and can be locked by clamping with those through screwing. Due to being guided in the oblong holes 8, 9, the two couplings 6, 7 can be positioned relative to each other in the direction A. The first coupling 5 is fluidically connected with a fresh dialysis fluid input line not shown in the figures and the second coupling 6 is connected with a used dialysis fluid output line also not shown in the figures.

FIG. 2 shows the connection area with an open disinfection flap 4. In this state the dialyzer 1 is inserted in the connection area as shown in FIG. 3. During this process, its dialysis fluid connection ports at the circumferential surface 10 thereof, that project outwards in radial direction and that cannot be seen in the figures, are plugged in/on or inserted each into the corresponding coupling 5, 6. When the purposeful end position of the dialyzer 1 at the housing 2 is reached, the dialysis fluid side of the dialyzer 1, the fresh dialysis fluid input line and the used dialysis fluid output line are fluidically connected with each other. Furthermore, the dialyzer 1 is held with its dialysis fluid connection ports in the couplings 5, 6 and is removably fixed in position at the housing 2. Apart from tubes/tubing 11 of the extracorporeal blood circuit, no tubes are present in the connection area, so that this area is very clearly arranged and neat.

The disinfection flap is movably attached at the housing 2 via a joint 12 (hinge). At that side facing the housing 2 in a closed state, the disinfection flap 4 is equipped with closure plugs 13, 14, that are adapted for an engagement and sealing of the couplings 5, 6. The closure plugs 13, 14 can according to one embodiment of the invention be formed as hollow plugs/hollow pins and can be connected with each other via a connection passage that is not shown in the figures and that is formed in the disinfection flap. In such an embodiment, the two couplings 5, 6 can be short-circuited by closing the disinfection flap 4 for example for the purpose of rinsing and cleaning.

The invention claimed is:

1. An extracorporeal blood treatment machine, the machine comprising:
 fluidics for a blood treatment fluid; and
 a machine housing at least in sections surrounding the fluidics;
  wherein the fluidics comprise an input line for supplying fresh blood treatment fluid to a filter and an output line for receiving used blood treatment fluid from the filter, the input line equipped with a first connection port for releasably coupling the filter to the machine-internal fluidics and the output line equipped with a second connection port for releasably coupling the filter to the machine-internal fluidics, and
  wherein the first connection port is formed as a first connection coupling integrated into the machine housing and the second connection port is formed as a second connection coupling integrated into the machine housing; and
 a lid element coupled to the machine housing, the lid element configured to engage the first and second connection couplings.

2. The machine of claim 1, wherein the lid element comprises a fluid passage configured to fluidly connect the first connection coupling with the second connection coupling, when the lid element is arranged at the machine housing in a manner to engage the first and second connection couplings.

3. The machine of claim 1, wherein the lid element is movably held at the machine housing by a joint or a hinge.

\* \* \* \* \*